(12) United States Patent
Krysan

(10) Patent No.: US 9,040,570 B2
(45) Date of Patent: May 26, 2015

(54) COMPOUNDS FOR ANTI-FUNGAL TREATMENT

(75) Inventor: Damian J. Krysan, Pittsford, NY (US)

(73) Assignee: University of Rochester, Rochester, NY (US)

(*) Notice: Subject to any disclaimer, the term of this patent is extended or adjusted under 35 U.S.C. 154(b) by 259 days.

(21) Appl. No.: 13/695,185

(22) PCT Filed: Apr. 29, 2011

(86) PCT No.: PCT/US2011/034627
§ 371 (c)(1),
(2), (4) Date: Mar. 14, 2013

(87) PCT Pub. No.: WO2011/137376
PCT Pub. Date: Nov. 3, 2011

(65) Prior Publication Data
US 2013/0172395 A1    Jul. 4, 2013

Related U.S. Application Data

(60) Provisional application No. 61/330,086, filed on Apr. 30, 2010.

(51) Int. Cl.
| | | |
|---|---|---|
| A61K 31/41 | (2006.01) | |
| A61K 31/135 | (2006.01) | |
| A61K 31/4196 | (2006.01) | |
| A61K 31/138 | (2006.01) | |

(52) U.S. Cl.
CPC ........... *A61K 31/4196* (2013.01); *A61K 31/135* (2013.01); *A61K 31/138* (2013.01); *A61K 31/41* (2013.01)

(58) Field of Classification Search
CPC ............ A61K 31/4196; A61K 31/138; A61K 2300/00
USPC .................................................. 514/383, 652
See application file for complete search history.

(56) References Cited

U.S. PATENT DOCUMENTS 5,605,700 A    2/1997 Degragorio

FOREIGN PATENT DOCUMENTS

WO    2004/002430 A2    1/2004

OTHER PUBLICATIONS

Krysan et al. Abstract of the Interscience Conference on Antimicrobial Agents and Chemotherapy, 2008, vol. 48, pp. 661, Meeting Info: 48th Annual Interscience Conference on Antimicrobial agents and Chemotherapy/46th Annual Meeting of the Infectous-Diseases-Society-of-America. Washington, D.C, USA. Oct. 25, 2008. CAPLUS Abstract, AN 2009:237073.*

International Search Report and Written Opinion for PCT/US2011/034627, mailed Jan. 19, 2012.

International Preliminary Report on Patentability for PCT/US2011/034627, mailed Nov. 15, 2012.

(Continued)

*Primary Examiner* — Shengjun Wang
(74) *Attorney, Agent, or Firm* — Kilpatrick Townsend & Stockton, LLP

(57) ABSTRACT

Provided are methods of treating or preventing a fungal infection in a subject. The methods comprise selecting a subject with or at risk of developing a fungal infection and administering to the subject a therapeutically effective amount of toremifene and fluconazole or derivatives thereof.

15 Claims, 9 Drawing Sheets

(56) References Cited

OTHER PUBLICATIONS

Supplementary European Search Report for EP 11775653 mailed Oct. 2, 2013.
Abruzzo, et al., "Evaluation of the Echinocandin Antifungal MK-0991 (L-743,872): Efficacies in Mouse Models of Disseminated Aspergillosis, Candidiasis, and Cryptococcosis," Antimicrobial Agents and Chemotherapy 41(11):2333-2338 (1997).
Bulatova et al. "Effect of Chemosensitizers on Minimum Inhibitory Concentrations of Fluconazole in Candida albicans," *Medical Principles and Practice* 17:117-121 (2008).
Butts, et al., "Estrogen Receptor Antagonists Are Anti-Cryptococcal Agents That Directly Bind EF Hand Proteins and Synergize with Fluconazole In Vivo," MBio 5(1):1-11 (2014).
Courchesne, "Characterization of a Novel, Broad-Based Fungicidal Activity for the Antiarrhythmic Drug Amiodarane," JPET, 300(1):195-199 (2002).
Dolan et al. "Antifungal Activity of Tamoxifen: In Vitro and In Vivo Activities and Mechanistic Characterization," *Antimicrobial Agents and Chemotherapy* 53(8):3337-3346 (2009).
Fries et al. "Phenotypic Switching of *Cryptococcus neoformans* Can Produce Variants That Elicit Increased Intracranial Pressure in a Rat Model of Cryptococcal meningoencephalitis," *Infection and Immunity* 73(3):1779-1787 (2005).
Gershanovich et al. "High-dose toremifene in advanced renal-cell carcinoma," *Cancer Chemother. Pharmacol* 39:547-551(1997).
Goldman, et al., "*Cryptococcus neoformans* meningitis in the rat," Lab Invest. 75(6):759-70 (1996).
Krysan, et al. "A High-Throughput Screening Assay for Small Molecules That Disrupt Yeast Cell Integrity," *J. Biomol Screen* 13(7):657-664 (2008).
Kuroda, et al., "Structural studies on some tamoxifen derivatives" J Med Chem. 28(10):1497-503 (1985).
Lara Jr. et al. "High-dose toremifene as a cisplatin modulator in metastatic non-small cell lung cancer: targeted plasma levels are achievable clinically," *Cancer Chemother. Pharmacol.* 42:504-508 (1998).
Morello et al. "Pharmacokinetics of selective estrogen receptor modulators," *Clin. Pharmacokinet.* 42:361-372 (2003).
National Committee for Clinical Laboratory Standards. "Reference method for broth dilution antifungal susceptibility testing of yeasts. Approved standard M27-A2," vol. 22(15). National Committee for Clinical Laboratory Standards. Wayne, PA. (2002).
Nosanchuk, et al., "Amphotericin B and Fluconazole Affect Cellular Charge, Macrophage Phagocytosis, and Cellular Morphology of *Cryptococcus neoformans* at Subinhibitory Concentrations," Antimicrobial Agents and Chemotherapy 43(2):233-239 (1999).
Rivera-Guevara C, et al., "Tamoxifen and its new derivatives in cancer research." Recent Pat Anticancer Drug Discov. 6(2):237-45 (2011).
Vu, et al., "Astemizole and an analogue promote fungicidal activity of fluconazole against *Cryptococcus neoformans* var. *grubii* and *Cryptococcus gattii*" 48(2):255-62. doi: 10.1080/13693780903081968 (2010).

* cited by examiner

Novel Antifungal Drugs Identified in AK Screen of Marketed Drugs

| Drug | Indication |
|---|---|
| Methiothepin | anti-depressant |
| Oxethazaine | anesthetic |
| Suloctidil | vasodilator |
| Vanoxevine | addiction therapy |
| Proadifen | CYP450 Inhibitor |
| Lidoflazine | calcium channel blocker |
| Felodipine | calcium channel blocker |
| Astemizole | anti-histamine |
| Sertaline | anti-depressant |
| Benfluorex | hypolipidemic |

Figure 3B

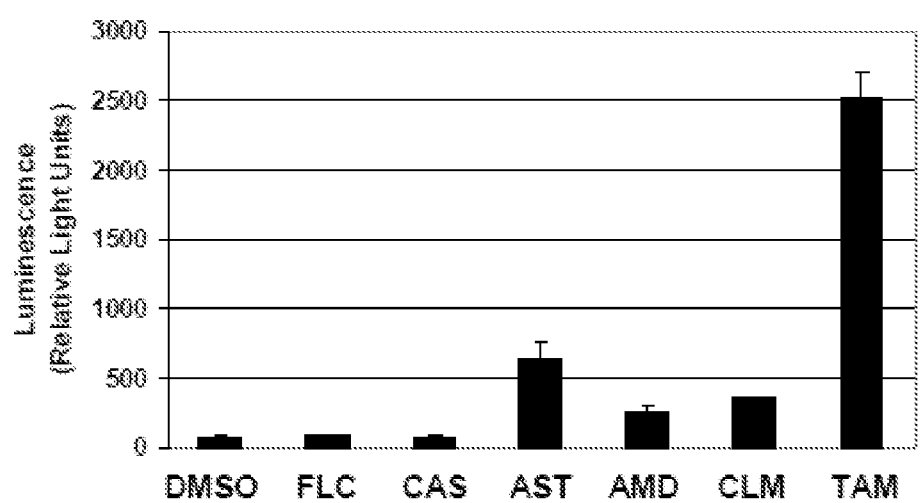

Figure 4

TABLE 2. MICs of TAM against S. cerevisiae, Candida, and C. neoformans.

| Species | Strain | TAM MIC (μg/mL)[a] | CLM MIC (μg/mL) |
|---|---|---|---|
| S. cerevisiae | BY4741 | 12 | 16 |
| C. albicans | ATCC 90028 | 32 | >64 |
| C. albicans | SC5314 | 32 | 32 |
| C. parapsilosis | R056-G12 | 64 | 64 |
| C. dubliniesis | CD1 | 16 | 32 |
| C. glabrata | MR084-G12 | 8 | 32 |
| C. tropicalis | MR084-H | 32 | 64 |
| C. neoformans | NYS 3-81 | 64 | 64 |
| C. neoformans | KN99 α | 64 | 64 |

[a]Endpoint defined as no turbidity by visual inspection following CLSI protocol. Data are based on at least two independent replicates performed on separate days in triplicate. All replicates of MIC determinations were within a two-fold dilution of the reported value.

Figure 5A

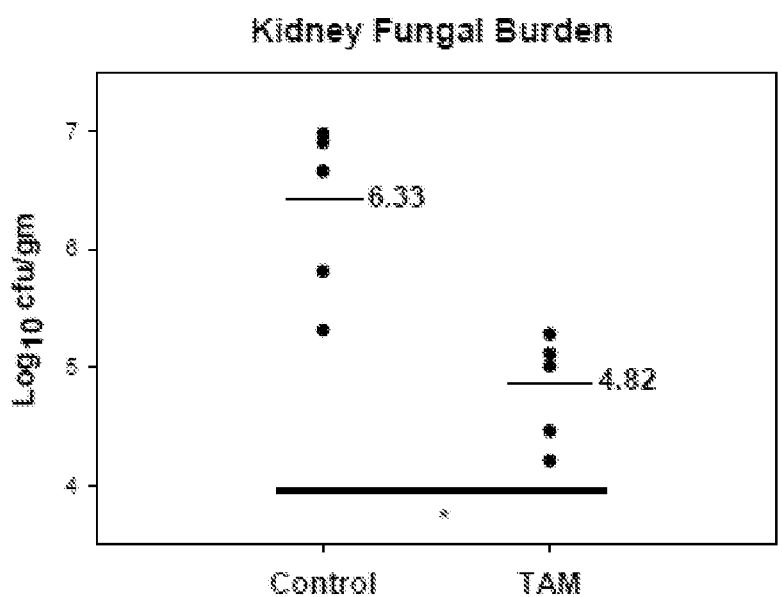

Figure 5B

Tamoxifen　　　Clomiphene　　　Toremifene

Classes of conditional separation of function calmodulin mutants.
- cmd1-226: actin cytoskeleton
- cmd1-228: Cmd1p localization
- cmd1-231: bud emergence
- cmd1-233: mitosis

COMPOUNDS FOR ANTI-FUNGAL TREATMENT

CROSS REFERENCE TO RELATED APPLICATIONS

This application claims the benefit of U.S. Provisional Application No. 61/330,086, filed on Apr. 30, 2010, which is hereby incorporated by reference in its entirety.

BACKGROUND

*Cryptococcus neoformans* is a fungal pathogen that causes pulmonary and central nervous system infections in immunocompromised and, less commonly, immunocompetent patients. *Cryptococcus neoformans* is an important cause of meningitis in patients with decreased immune function (HIV/AIDS, cancer patients, and organ transplant patients). Current standard of care therapy for this infection requires toxic agents that must be given intravenously. Oral alternatives are available; however, these alternatives are much less effective because they fail to directly kill *C. neoformans*.

SUMMARY

Provided herein are methods of treating or preventing a fungal infection in a subject. The methods comprise selecting a subject with or at risk of developing a fungal infection and administering to the subject a therapeutically effective amount of toremifene and fluconazole or derivatives thereof.

The details of one or more embodiments are set forth in the accompanying drawings and the description below. Other features, objects, and advantages of the invention will be apparent from the description and drawings, and from the claims.

DESCRIPTION OF DRAWINGS

FIGS. 2A and 2B are graphs demonstrating a dose response of caspofungin (CAS) with *S. cerevisiae* cells evaluated by the AK assay (FIG. 2A) and a growth assay (FIG. 2B). The minimum inhibitory concentration (MIC) for this strain of *S. cerevisiae* cells is 62 ng/ml.

FIGS. 3A and 3B show an AK assay screen of a library of marketed drugs demonstrating activity against *C. neoformans*. FIG. 3A shows a graph representing an example screening plate from a *S. cerevisiae*/AK screen of a library of marketed drugs. The numbered data points indicate compounds scored as positive. FIG. 3B shows a table of ten previously marketed drugs with unknown antifungal activity identified in the AK assay screen.

FIG. 4 shows a graph demonstrating that the AK assay detects lysis in *C. neoformans*. Log phase *C. neoformans* cells were treated with DMSO (1%), fluconazole (FLC, 16 μg/ml), caspofungin (CAS, 250 ng/ml), astemizole (AST, 50 μg/ml), Amiodarone (AMD, 50 μg/ml), clomiphene (CLM, 64 μg/ml), and tamoxifen (TAM, 64 μg/ml).

FIGS. 5A and 5B show in vitro and in vivo antifungal activity of TAM/CLM. FIG. 5A shows a table demonstrating the minimum inhibitory concentration (MIC) of TAM and CLM against a variety of pathogenic yeasts determined using CLSI-approved methods. FIG. 5B shows a graph demonstrating the in vivo activity of TAM in a tail vein injection model of disseminated candidiasis with 48 hour kidney fungal burden as the endpoint following a 7 day pre-treatment with TAM at 200 mg/kg or placebo. *Indicates P<0.05 using Mann-Whitney test.

FIG. 7A shows a graph demonstrating AK activity of clomiphene (CLM), tamoxifen (TAM), and toremifene (TOR). FIG. 7B shows a graph demonstrating the minimum inhibitory concentration (MIC) of TAM, CLM, and TOR. The serum level of TOR is indicated by the bar.

FIG. 8A shows that *S. cerevisiae* strains overexpressing PKC1 have increased sensitivity to TAM. FIG. 8B shows that overexpression of calmodulin 1 (CMD1) increase the tolerance to TAM. FIG. 8C shows the classes of hypofunctional *S. cerevisiae* cmd1 mutants. FIG. 8D shows that the hypofunctional cmd1 mutants are hypersensitive to TAM.

FIG. 9A shows an image of a Western blot of immunoprecipitated Myo2p in the presence and absence of TAM and the known calmodulin inhibitor pro-chlorpromazine (PRO). FIG. 9B shows a graph demonstrating a semiquantitation of the Western blot of FIG. 9A. FIG. 9C shows an image demonstrating that Myo2-GFP does not localize to septum in TAM-treated cells.

DETAILED DESCRIPTION

Figure 1:
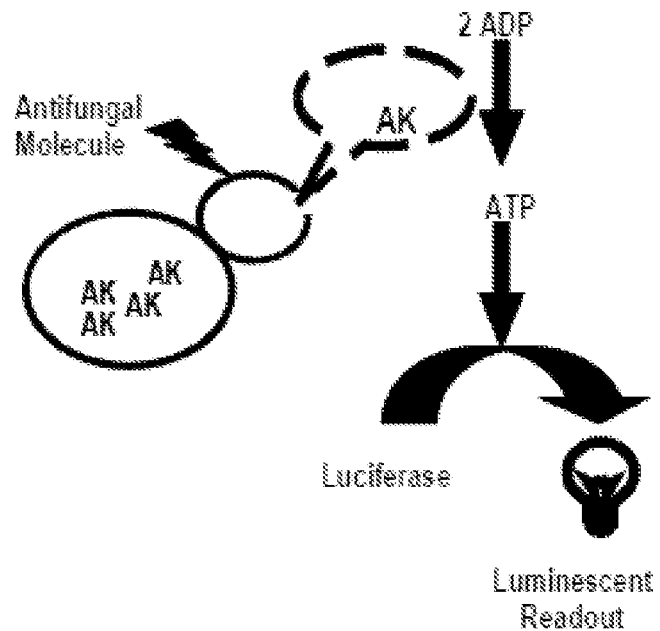
FIG. 1 shows a schematic of the adenylate kinase (AK) assay used to identify chemicals capable of causing yeast cell lysis.

Provided herein are methods of treating or preventing a fungal infection in a subject. The methods comprise selecting a subject with or at risk of developing a fungal infection and administering to the subject a therapeutically effective amount of toremifene and fluconazole or derivatives thereof. The methods can further comprise administering to the subject a therapeutically effective amount of tamoxifen or clomiphene or derivatives thereof.

The fungal infection can be, but is not limited to, an infection caused by a fungus selected from the group consisting of *Saccharomyces cerevisiae, Candica albicans*, or *Cryptococcus neoformans*.

In the methods described throughout, toremifene, fluconazole, tamoxifen or clomiphene are used as examples. Derivatives having anti-fungal effects can be used similarly. Tamoxifen derivatives are described, for example, in Kurado et al. (1995) Structural studies on some tamoxifen derivatives, J. Med. Chem. 28:1497-1503; Rivera-Guevara and Camacho, (2011), Tamoxifen and its derivatives in cancer research. One of skill in the art can assess the anti-fungal effects of such derivatives using methods taught herein.

The subject is administered a therapeutically effective amount of toremifene. The subject can, for example, be administered a dose of toremifene, wherein the dose ranges from about 2 micrograms per milliliter (µg/ml) to about 20 µg/ml. Optionally, the subject is administered a 4 µg/ml dose of toremifene. Optionally, the subject is administered a 2 µg/ml dose of toremifene. Optionally, the subject is administered at least 60 milligrams of toremifene. Optionally, the subject is administered about 60 to about 600 milligrams of toremifene. Optionally, the subject is administered 300 milligrams of toremifene in one administration or in multiple administrations. Administrations can be repeated as necessary or desired.

The subject is administered a therapeutically effective amount of fluconazole. The subject can, for example, be administered a dose of fluconazole, wherein the dose ranges from about 2 µg/ml to about 20 µg/ml. Optionally, the subject is administered a 4 µg/ml dose of fluconazole. Optionally, the subject is administered a 2 µg/ml dose of fluconazole. Optionally, the subject is administered at least 100 milligrams of fluconazole. Optionally, the subject is administered about 100 to about 1000 milligrams of fluconazole in one administration or in multiple adminsitrations. Administrations can be repeated as necessary or desired.

Optionally, the subject is administered a therapeutically effective amount of tamoxifen and/or clomiphene. The subject can, for example, be administered a dose of tamoxifen and/or clomiphene, wherein the dose ranges from about 2 µg/ml to about 20 µg/ml. Optionally, the subject is administered at least 60 milligrams of tamoxifen and/or clomiphene. Optionally, the subject is administered about 60 to about 600 milligrams of tamoxifen and/or clomiphene.

Provided herein are compositions containing the provided compounds (e.g., toremifene, fluconazole, tamoxifen, and clomiphene) and a pharmaceutically acceptable carrier described herein. The herein provided compositions are suitable for administration in vitro or in vivo. By pharmaceutically acceptable carrier is meant a material that is not biologically or otherwise undesirable, i.e., the material is administered to a subject without causing undesirable biological effects or interacting in a deleterious manner with the other components of the pharmaceutical composition in which it is contained. The carrier is selected to minimize degradation of the active ingredient and to minimize adverse side effects in the subject.

Suitable carriers and their formulations are described in *Remington: The Science and Practice of Pharmacy*, 21$^{st}$ Edition, David B. Troy, ed., Lippicott Williams & Wilkins (2005). Typically, an appropriate amount of a pharmaceutically-acceptable salt is used in the formulation to render the formulation isotonic. Examples of the pharmaceutically-acceptable carriers include, but are not limited to, sterile water, saline, buffered solutions like Ringer's solution, and dextrose solution. The pH of the solution is generally about 5 to about 8 or from about 7 to 7.5. Other carriers include sustained release preparations such as semipermeable matrices of solid hydrophobic polymers containing the immunogenic polypeptides. Matrices are in the form of shaped articles, e.g., films, liposomes, or microparticles. Certain carriers may be more preferable depending upon, for instance, the route of administration and concentration of composition being administered. Carriers are those suitable for administration of the agent, e.g., the small molecule, polypeptide, nucleic acid molecule, and/or peptidomimetic, to humans or other subjects.

The compositions are administered in a number of ways depending on whether local or systemic treatment is desired, and on the area to be treated. The compositions are administered via any of several routes of administration, including topically, orally, parenterally, intravenously, intra-articularly, intraperitoneally, intramuscularly, subcutaneously, intracavity, transdermally, intrahepatically, intracranially, nebulization/inhalation, or by installation via bronchoscopy. Optionally, the composition is administered by oral inhalation, nasal inhalation, or intranasal mucosal administration. Administration of the compositions by inhalant can be through the nose or mouth via delivery by spraying or droplet mechanism, for example, in the form of an aerosol.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives are optionally present such as, for example, antimicrobials, antioxidants, chelating agents, and inert gases and the like.

Formulations for topical administration include ointments, lotions, creams, gels, drops, suppositories, sprays, liquids, and powders. Conventional pharmaceutical carriers, aqueous, powder, or oily bases, thickeners and the like are optionally necessary or desirable.

Compositions for oral administration include powders or granules, suspension or solutions in water or non-aqueous media, capsules, sachets, or tables. Thickeners, flavorings, diluents, emulsifiers, dispersing aids or binders are optionally desirable.

The aforementioned second therapeutic agents, tamoxifen and/or clomiphene, can be used in any combination with the compositions described herein. Combinations are administered either concomitantly (e.g., as an admixture), separately but simultaneously (e.g., via separate intravenous lines into the same subject), or sequentially (e.g., one of the compounds is given first followed by the second). Thus, the term combination is used to refer to concomitant, simultaneous, or sequential administration of two or more agents.

As used throughout, subject can be a vertebrate, more specifically a mammal (e.g., a human, horse, cat, dog, cow, pig, sheep, goat, mouse, rabbit, rat, and guinea pig), birds, reptiles, amphibians, fish, and any other animal. The term does not denote a particular age or sex. Thus, adult and newborn subjects, whether male or female, are intended to be covered. As used herein, patient or subject may be used interchangeably and can refer to a subject with a fungal infection (e.g., infection with *C. neoformans*). The term patient or subject includes human and veterinary subjects.

A subject at risk of developing a fungal infection can, for example, have risk factors for fungal infections (e.g., have damaged or moist skin, have chronic disease, and/or be immunocompromised). A subject at risk for developing a fungal infection can, for example, be exposed to a fungus due to employment (e.g., a health care worker) or due to the prevalence of a fungus at a specific location (e.g., a hospital). A subject currently with a fungal infection has one or more than one symptom of the infection and may have been diagnosed with the fungal infection.

The methods and agents as described herein are useful for both prophylactic and therapeutic treatment. For prophylactic use, a therapeutically effective amount of the agents described herein are administered to a subject prior to onset (e.g., before contracting a fungal infection) or during early onset (e.g., upon initial signs and symptoms of a fungal infection). Prophylactic administration can occur for several days to years prior to the manifestation of symptoms of a fungal infection. Prophylactic administration can be used, for example, in the preventative treatment of subjects at risk for developing a fungal infection. Therapeutic treatment involves administering to a subject a therapeutically effective amount of the compounds described herein after diagnosis or development of a fungal infection.

According to the methods taught herein, the subject is administered an effective amount of the agent. The terms effective amount and effective dosage are used interchangeably. The term effective amount is defined as any amount necessary to produce a desired physiologic response (e.g., reduction or elimination of fungal infection). Effective amounts and schedules for administering the compounds may be determined empirically, and making such determinations is within the skill in the art. The dosage ranges for administration are those large enough to produce the desired effect in which one or more symptoms of the fungal infection are affected (e.g., reduced or delayed). The dosage should not be so large as to cause substantial adverse side effects, such as unwanted cross-reactions, anaphylactic reactions, and the like. Generally, the dosage will vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary, and can be administered in one or more dose administrations daily, for one or several days. Guidance can be found in the literature for appropriate dosages for given classes of pharmaceutical products.

As used herein the terms treatment, treat, or treating refers to a method of reducing the effects of a fungal infection or symptom of the fungal infection. Thus in the disclosed method, treatment can refer to a 10%, 20%, 30%, 40%, 50%, 60%, 70%, 80%, 90%, or 100% reduction in the severity of an established fungal infection or symptom of the infection. For example, a method for treating a fungal infection is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the infection, condition, or symptoms of the infection or condition.

As used herein, the terms prevent, preventing, and prevention of a fungal infection refers to an action, for example, administration of a compound described herein, that occurs before or at about the same time a subject begins to show one or more symptoms of the fungal infection, which inhibits or delays onset or exacerbation of one or more symptoms of the fungal infection. As used herein, references to decreasing, reducing, or inhibiting include a change of 10%, 20%, 30%, 40%, 50%, 60%, 70%, 80%, 90% or greater as compared to a control level. Such terms can include but do not necessarily include complete elimination.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

Example 1

High-throughput Assay for Identifying Chemicals Capable of Causing Yeast Cell Lysis A high throughput assay that detects molecules that cause yeast cell lysis was recently developed as a new method for anti-fungal drug discovery (Krysan and DiDone, J. Biomol. Screen 13:657-64 (2008)). The adenylate kinase (AK) assay has three important features that make it a very useful tool for the identification of fungicidal anti-cryptococcal molecules: it is specific for fungicidal molecules; it is cell-based; and it is carried out with C. neoformans directly.

The AK assay was designed to take advantage of the fact that dead yeast cells lose membrane integrity and leak intracellular enzymes and proteins into culture medium. Upon cell lysis, AK is released into the medium and is detected by a coupled enzyme reaction in which AK converts 2 molecules of ADP into ATP. The ATP and luciferin are used by luciferase and a luminescent signal is generated as a reporter of yeast cell lysis (FIG. 1). The AK assay is specific for molecules that are fungicidal and is more sensitive than traditional growth-based antifungal screening assays. Additionally, traditional growth-based screening cannot differentiate between fungistatic and fungicidal molecules. Since fungicidal molecules are much more effective for the treatment of cryptococcosis, AK-based screening allows for the direct detection of molecules of highest interest in terms of further development.

Figure 2A:
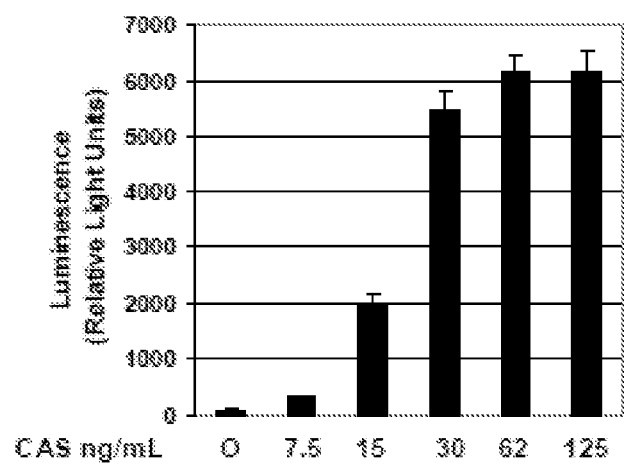
FIGS. 2A and 2B show characteristics of the AK assay.
Figure 2B:
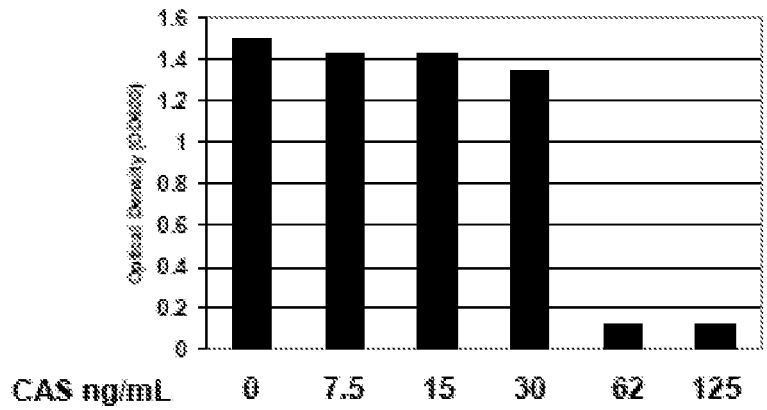

For molecules that cause cell lysis, the AK assay is much more sensitive than growth assays as demonstrated by the fact that caspofungin (CAS) induces AK release at concentrations ~10 fold below the concentration that causes detectable change in growth rate (compare FIGS. 2A and 2B). This is because a significant proportion of yeast cells can undergo lysis without an apparent change in growth rate, which is a function of the logarithmic nature of yeast growth. The improved sensitivity of the AK assay as compared to traditional growth assay-based screening means that weakly active molecules will be more easily detected, allowing the identification of molecular scaffolds that can then be optimized through medicinal chemistry.

As previously described, the AK assay is also specific for fungicidal molecules (Krysan and DiDone, J. Biomol. Screen 13:657-64 (2008)). For example, fungistatic molecules such as fluconazole (FLC) and griseofulvin do not cause lysis and are negative in the AK assay. This specificity is particularly well suited for the identification of new anti-cryptococcal molecules because fungicidal molecules are clinically much more effective than fungistatic drugs.

Example 2

AK-based Screen of a Library of Previously Marketed Drugs Identifies Novel Fungicidal Molecules The AK assay performs well in the high throughput screen (HTS) setting because it is amenable to 384-well format (Krysan and DiDone, J. Biomol. Screen 13:657-64 (2008)), logistically simple, and uses commercially available reagents. The AK assay provides Z' scores of 0.7-0.9 (Z' scores range from 0-1.0 with Z'>0.5 generally required for an assay to be suitable for HTS and excellent assays give scores of 0.7-1.0).

Figure 3A:
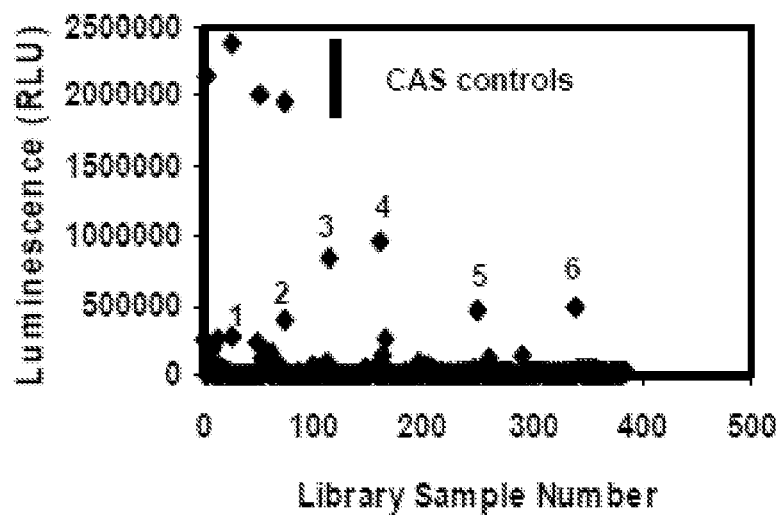

As part of the validation studies, a library of 1200 previously marketed drugs (Prestwick Library) was screened using the AK assay with *S. cerevisiae* (Krysan and DiDone, J. Biomol. Screen 13:657-64 (2008)). The raw data taken from one of the plates in this screen is shown in FIG. 3A. The library contained 15 clinically used antifungal drugs, of which 9 scored positive as fungilytic. The antifungal molecules that were not positive (e.g. fluconazole and griseofulvin) have fungistatic activity, confirming the specificity of AK assay for fungicidal drugs in the HTS setting. In addition to molecules with known antifungal activity, fungilytic activity was identified in 10 drugs for which no antifungal activity had been reported previously (FIG. 3B). Subsequently, the antifungal activity of two drugs, astemizole and suloctidil was confirmed by other laboratories (Vu and Gelli, Med. Mycol. 1-9 (2009)). Thus, the AK assay is a sensitive reporter of antifungal activity in the HTS setting.

Example 3

The AK Assay Identifies Fungilytic Molecules in *C. Neoformans*

In order to determine whether the AK assay was applicable to *C. neoformans*, a set of molecules containing drugs was tested. The set of molecules contained drugs with known fungicidal activity (amiodarone) (Courchesne, J. Pharmacol. Exper. Ther. 300:195-9 (2002)), with fungistatic activity (fluconazole), with poor clinical activity (caspofungin) Abruzzo et al., Antimicrob. Agents Chemother. 41:2333-8 (1997)), and molecules identified in the *S. cerevisiae* AK screen (astemizole, tamoxifen and clomiphene). Using the same protocol that has proven successful with other yeast, AK release was detected for molecules known to be fungicidal (amiodarone) and not for molecules that are either fungistatic (FLC) or poorly active (CAS) (FIG. 4). These data demonstrate that the AK assay is not affected by the presence of the extracellular capsule in *C. neoformans*. As expected, the AK assay is specific for molecules that are fungicidal toward *C. neoformans*. Furthermore, this experiment demonstrated that three molecules identified in the *S. cerevisiae* based screen (tamoxifen, clomiphene and astemizole) also caused lysis in *C. neoformans*. While these studies were in progress, it was reported that astemizole is also fungicidal toward *C. neoformans* and is synergistic with FLC (Vu and Gelli, Med. Mycol. 1-9 (2009)). Taken together, these data demonstrate that the AK assay is a useful tool for identifying new anti-cryptococcal molecules and suggest that screening libraries of previously marketed drugs may reveal new agents for the treatment of cryptococcosis.

Example 4

Tamoxifen and Structurally-related Estrogen Receptor Antagonists are Fungicidal Molecules Although the antifungal activity of tamoxifen was initially described in *C. albicans* and *S. cerevisiae* over twenty years ago, it was not further characterized using standardized susceptibility methods or by in vivo testing in animal models. As discussed above, tamoxifen and the structurally related molecule clomiphene were identified as highly fungilytic by screening a library of previously marketed molecules using the AK assay with *S. cerevisiae*. Follow-up assays showed that tamoxifen and clomiphene also cause lysis of *C. albicans* and *C. neoformans*. To further characterize the antifungal activity of tamoxifen and clomiphene (Dolan et al., Antimicrob. Agents Chemother. 53:3337-46 (2009)), in vitro susceptibility testing was performed with a range of pathogenic yeast using CLSI standardized methods (FIG. 5A). Both molecules were active toward these species with activity varying from 8 µg/mL for *C. glabrata* to 64 µg/mL for *C. neoformans* with clomiphene being consistently less active than tamoxifen.

To characterize the in vivo activity of tamoxifen, a mouse model of disseminated candidiasis was used. Mice were treated with either sham or tamoxifen for seven days prior to challenge with *C. albicans* by tail vein injection. The pretreatment was necessary to establish serum levels comparable to that achieved in humans following a single dose. The mice were treated for an additional two days, sacrificed, and kidney fungal burdens determined. Kidney fungal burden is a well-characterized quantitative endpoint that correlates with efficacy. As shown in FIG. 5B, tamoxifen treatment lowered fungal burdens 1.5 $\log_{10}$, indicating that it has significant in vivo activity. These studies further support the potential utility of this class of molecules as antifungal agents.

Example 5

Figure 6:
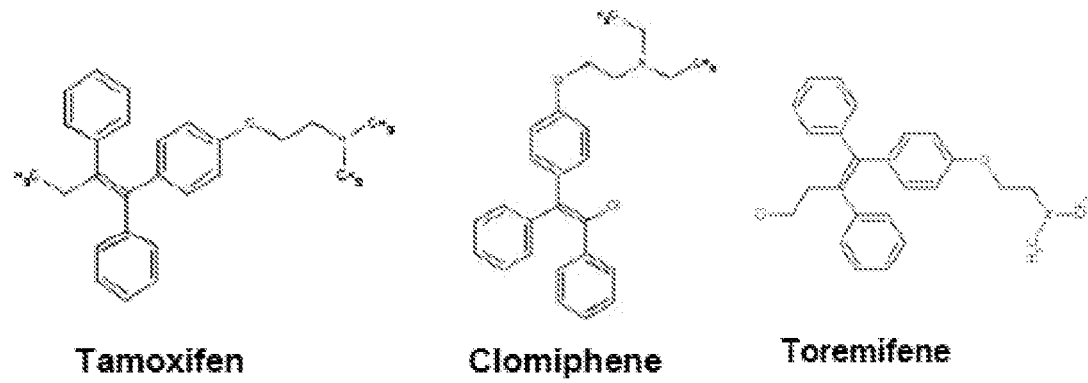
FIG. 6 shows the structures of estrogen receptor antagonists with antifungal activity. Shown are tamoxifen (TAM), clomiphene (CLM), and toremifene (TOR).
Figure 7A:
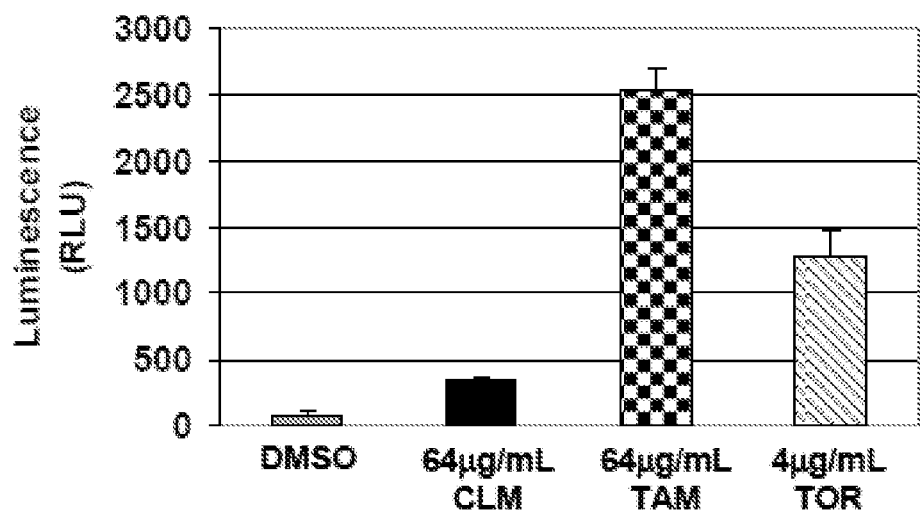
FIGS. 7A and 7B shows a comparison the in vitro activity of tamoxifen (TAM) analogs against *C. neoformans*.
Figure 7B:
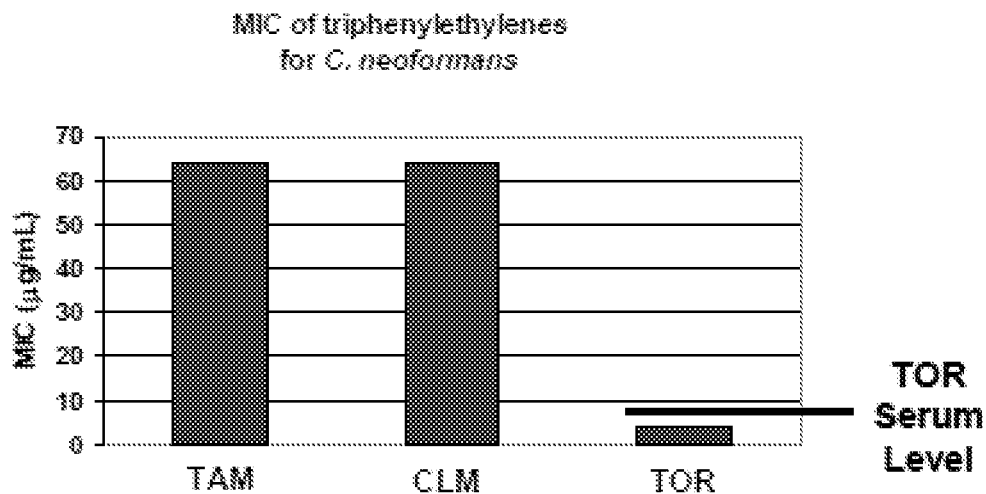

Toremifene is Active Against *C. Neoformans* at Concentrations Safely Achievable in Humans To complete the characterization of the antifungal activity of triphenylethylene-based estrogen receptor antagonists, toremifene was also evaluated. Toremifene is closely related to tamoxifen with the only difference being a chloride substituent (FIG. 6). Toward *C. albicans*, the activity of toremifene is identical to tamoxifen (MIC 32 µg/mL). However, toremifene is strikingly more active toward *C. neoformans* when compared to tamoxifen by AK assay (FIG. 7A) with a 12-fold increase in AK release at 4 µg/mL. Consistent with the increased AK release at lower concentrations (FIG. 7B), the MIC for toremifene (4 µg/mL) against *C. neoformans* is 16-fold lower than either tamoxifen (64 µg/mL) or clomiphene (64 µg/mL). Reducing the temperature of incubation to 30° C. increased the MIC 2-fold (8 m/mL) relative to the MIC at 37° C. (4 m/mL), suggesting that it may affect pathways that contribute to high temperature growth. The interaction of toremifene with FLC was also evaluated using checkerboard methods. In *C. neoformans* with a FLC MIC of 4 µg/mL, the combination of 2 µg/mL of FLC and 2 µg/mL of toremifene completely inhibits growth, indicating an additive interaction with a Fractional Inhibitory Concentration (FIC)

of 1.0 with *C. neoformans*. The concentration at which toremifene is active alone or in combination with FLC is below the serum levels of toremifene that are achievable by oral dosing. Therefore, it represents an attractive lead compound for the treatment of cryptococcosis and, if shown to have in vivo efficacy, could be rapidly translated to clinical studies.

Example 6

Tamoxifen Targets Calmodulin in Yeast as Part of its Mechanism of Action

Figure 8A:
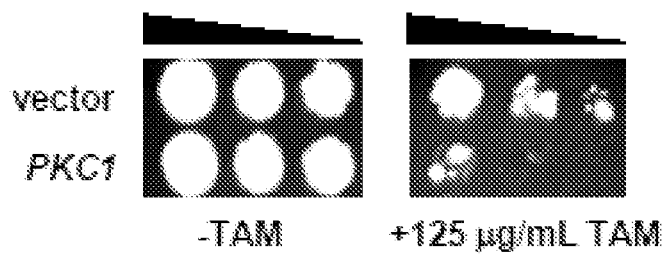
FIGS. 8A-8D show the chemical genetic analysis of protein kinase C (PKC) and calmodulin as targets of tamoxifen (TAM).
Figure 8B:
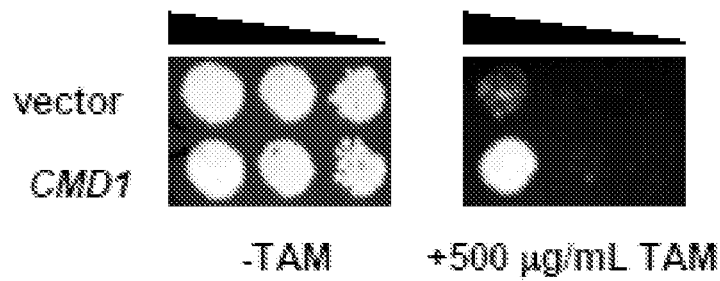
Figures 8C, 8D:
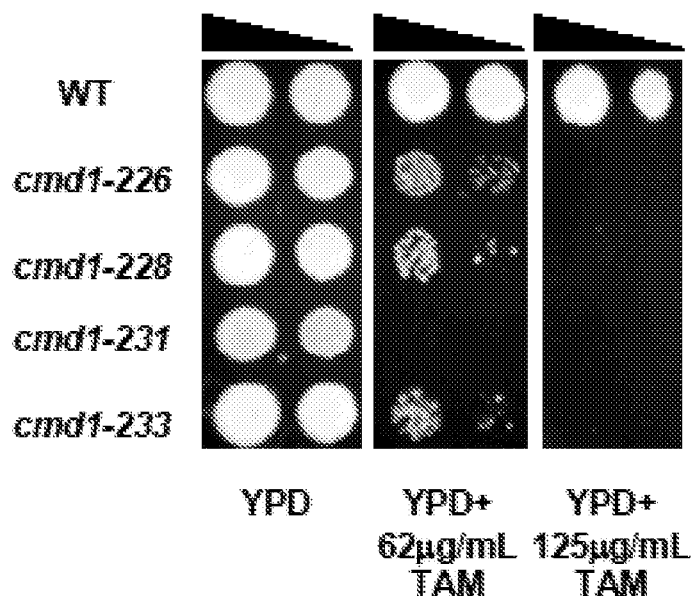

Previously, the molecular target of tamoxifen and related compounds in yeast was unknown. The mechanism of action for the antifungal activity of tamoxifen has been investigated (Dolan et al., Antimicrob. Agents Chemother. 53:3337-46 (2009)). Tamoxifen and its structurally related analogs have a number of biological activities in addition to their estrogen receptor antagonist properties. For example, tamoxifen is a well known inhibitor of protein kinase C and calmodulin. Both of these proteins are essential in yeast. Therefore, inhibition of these proteins was tested to determine if these proteins contribute to the antifungal activity of tamoxifen. The genes for protein kinase C (PKC1) and calmodulin (CMD1) were overexpressed in wild type *S. cerevisiae* and their growth was compared to vector transformed cells on plates supplemented with tamoxifen. Overexpression of PKC1 exacerbated its effects (FIG. 8A). On the other hand, overexpression of CMD1 suppressed toxicity (FIG. 8B), suggesting that calmodulin is involved in antifungal activity of tamoxifen. Further supporting calmodulin as a target of tamoxifen in yeast was the observation that strains with hypofunctional alleles of CMD1 were hypersensitive to tamoxifen (FIGS. 8C and 8D).

Figure 9A:
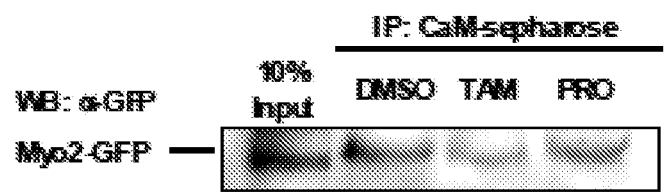
FIGS. 9A-9C show that tamoxifen (TAM) disrupts binding of calmodulin to Myo-2-GFP in vitro and causes Myo2 mislocalization.
Figure 9B:
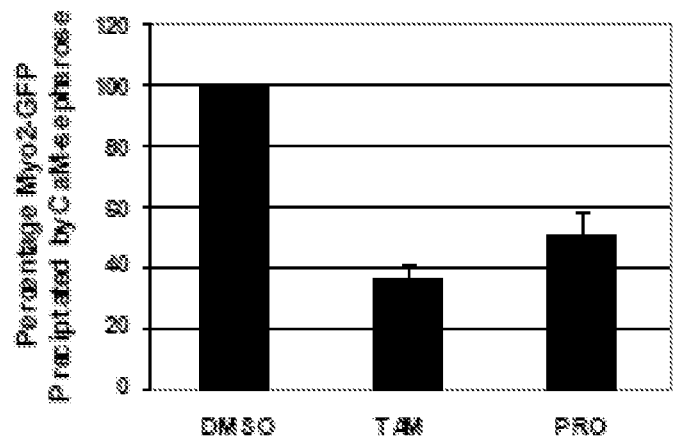
Figure 9C:
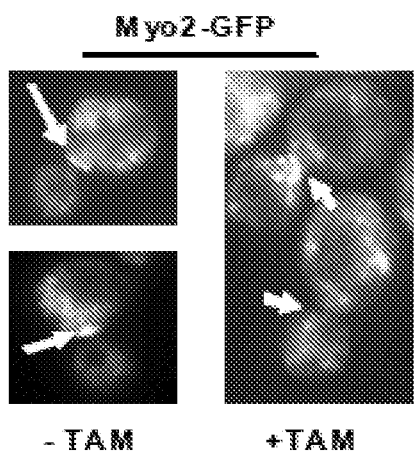

To more directly test the ability of tamoxifen to target calmodulin in yeast, the ability of tamoxifen to disrupt the interaction of calmodulin with one of its key binding partners, the myosin, Myo2p, was investigated. In vitro, tamoxifen interferes with the ability of sepharose bead immobilized calmodulin to pull down Myo2-GFP from crude yeast cell lysates (FIGS. 9A and 9B). Additionally, tamoxifen prevented Myo2-GFP from localizing to the bud neck/septum region during mitosis (FIG. 9C). Since this localization is dependent on Cmd1-Myo2p interactions, this demonstrates that at least part of the antifungal activity of tamoxifen is due to calmodulin antagonism.

Example 7

Effect of Toremifene on the Interaction of Macrophages with *C. neoformans*

Figure 10:
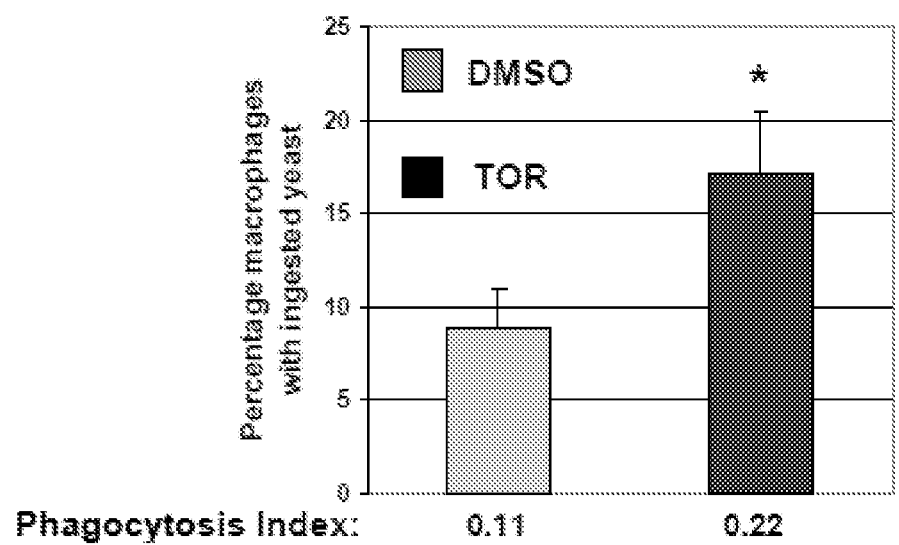
FIG. 10 shows a graph demonstrating that Toremifene (TOR) treatment increase non-antibody mediated phagocytosis of *C. neoformans* by J774 cells. *C. neoformans* JEC21 cells were treated overnight with DMSO or subinhibitory toremifene (4 μg/ml), washed, and exposed to J774 macrophage cells for 2 hours without antibody. Percentage phagocytosis and phagocytosis index were determined as described by Nosanchuk et al (Nosanchuk et al., Antimicrob. Agents Chemother. 43:233-9 (1999)). *P=0.03 by Student's T test.

Fluconazole and amphotericin B both increase the efficiency by which macrophages phagocytose *C. neoformans*. To determine whether toremifene treatment also increases phagocytosis of *C. neoforman*, the ability of murine macrophage-like cells J774 cells to ingest treated and untreated *C. neoformans* was compared. Following the protocol of Nosanchuk et al., an experiment shown in FIG. 10 indicates that toremifene treatment increases the ability of J774 cells to phagocytose *C. neoformans* 2-fold in the absence of opsonization (Nosanchuk et al., Antimicrob. Agents Chemother. 43:233-9 (1999)). For comparison, fluconazole increased phagocytosis by 2-fold as well (Nosanchuk et al., Antimicrob. Agents Chemother. 43:233-9 (1999)).

Example 8

In vivo Effect of Toremifene in Combination with Fluconazole

Utilizing a well established rat model of cryptococcal meningitis (Goldman et al., Lab. Investig. 75:759-70 (1996); Goldman et al., J. Med. Vet. Mycol. 35(4):271-8 (1997); Fries et al., Infect. Immun. 73(3):1779-87 (2005)), maximum tolerated doses of toremifene are tested. The rats are divided into multiple groups. Each group of rats with cryptococcal meningitis is administered varying doses of toremifene to determine the maximum tolerated dose that reduces the cryptococcal infection. A control group of rats receives no toremifene. The toremifene can be administered orally or intraperitoneally.

Once the maximum tolerated dose is determined, using the same rat model of cryptococcal meningitis, the maximum tolerated dose of toremifene is administered with varying doses of fluconazole to determine the in vivo synergistic effect of the two compounds in treating cryptococcal infection. The rats are divided into multiple groups. Each group of rats with cryptococcal meningitis is administered the maximum tolerated dose of toremifene, and each group is administered increasing doses of fluconazole. A control group of rats receives no fluconazole. Toremifene and fluconazole can be administered to the rats orally or intraperiotenally.

Varying doses of each of toremifene and fluconazole are tested similarly using various treatment regimens. For example, selected doses are administered daily for 2, 3, 4, 5, 6, 7, 8, 9, 10, or 20 days.

In all examples, the effect on cryptococcal meningitis is assessed by a skilled artisan using routine methods. For example, fungal burdens of cerebrospinal fluid (CSF) samples or organ samples are determined. CSF is obtained at the time of killing by puncture of the cistern magna. Lung and brain tissues are homogenized in 10 ml of PBS. One hundred μls of the CSF samples or tissue homogenates are plated on Sabouraud agar dextrose culture (SDA) medium for fungi. Colonies are counted after 72 to 96 h (one colony represents 1 CFU).

What is claimed is:

1. A method of treating a fungal infection in a subject in need thereof, the method comprising administering to the subject a therapeutically effective amount of toremifene and fluconazole, wherein the fungal infection is caused by *Cryptococcus neoformans*.

2. The method of claim 1, wherein the method further comprises selecting a subject with a fungal infection.

3. The method of claim 1, wherein the subject is administered a dose of toremifene, wherein the dose ranges from about 2 micrograms per milliliter (μg/ml) to about 20 μg/ml.

4. The method of claim 3, wherein the subject is administered a 4 μg/ml dose of toremifene.

5. The method of claim 3, wherein the subject is administered a 2 μg/ml dose of toremifene.

6. The method of claim 1, wherein the subject is administered at least 60 milligrams of toremifene.

7. The method of claim 1, wherein the subject is administered about 60 to about 600 milligrams of toremifene.

8. The method of claim 1, wherein the subject is administered a dose of fluconazole, wherein the dose ranges from about 2 μg/ml to about 20 μg/ml.

9. The method of claim 8, wherein the subject is administered a 4 μg/ml dose of fluconazole.

10. The method of claim 8, wherein the subject is administered a 2 μg/ml dose of fluconazole.

11. The method of claim 1, wherein the subject is administered at least 100 milligrams of fluconazole.

12. The method of claim 1, wherein the subject is administered about 100 to about 1000 milligrams of fluconazole.

13. The method of claim 1, wherein the therapeutically effective combination of toremifene and fluconazole is administered to the subject by a method selected from the group consisting of intravenous administration, intraperitoneal administration, oral administration, topical administration, intra-articular administration, mebulization/inhalation, and subcutaneous administration.

14. The method of claim 1, wherein the method further comprises administering to the subject a therapeutically effective amount of tamoxifen.

15. The method of claim 1, wherein the method further comprises administering to the subject a therapeutically effective amount of clomiphene.

\* \* \* \* \*